United States Patent [19]

dinh Can

[11] Patent Number: 4,488,393
[45] Date of Patent: Dec. 18, 1984

[54] METHOD FOR PACKAGING STERILE ACUPUNCTURE NEEDLES

[76] Inventor: Tran dinh Can, 20, Avenue de Friedland, 75008 Paris, France

[21] Appl. No.: 360,081

[22] Filed: Mar. 19, 1982

[30] Foreign Application Priority Data

Mar. 20, 1981 [FR] France .................. 81 05569

[51] Int. Cl.³ .............................................. B65B 9/00
[52] U.S. Cl. ........................................ 53/450; 53/555; 53/594
[58] Field of Search ................. 53/450, 555, 594, 397; 206/63.3, 366, 380

[56] References Cited

U.S. PATENT DOCUMENTS

| 2,705,857 | 4/1955 | Fox | 53/594 X |
| 4,345,415 | 8/1982 | Jarund | 53/450 |
| 4,384,441 | 5/1983 | Maruyama | 53/553 |
| 4,386,697 | 6/1983 | Zocher | 53/397 X |

Primary Examiner—A. J. Heinz
Attorney, Agent, or Firm—Pollock, Vande Sande & Priddy

[57] ABSTRACT

Two overlying continuous strips hermetically seal the needle portions of parallel adjacent acupuncture needles while the handle portions thereof remain exposed to permit the needle to be withdrawn. Serrations are formed between individually packaged needles so that the needles may be folded therealong and removed in a selected number from a continuous strip package.

2 Claims, 6 Drawing Figures

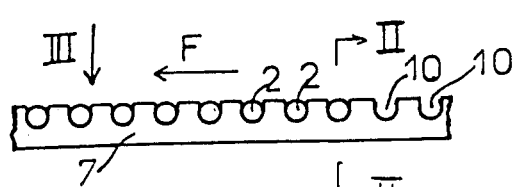
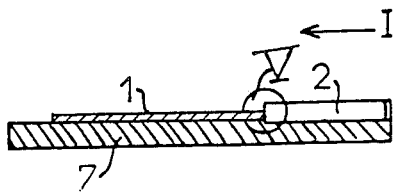
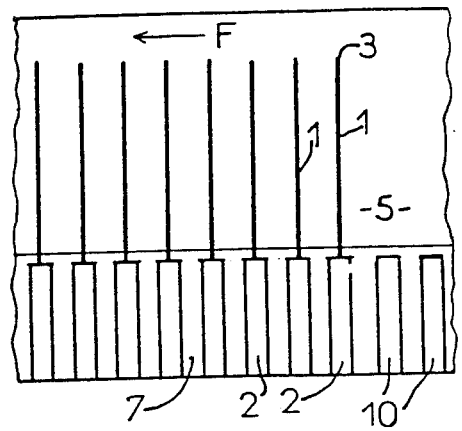
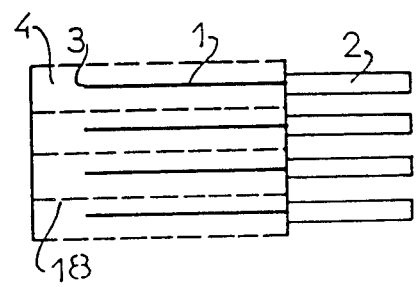
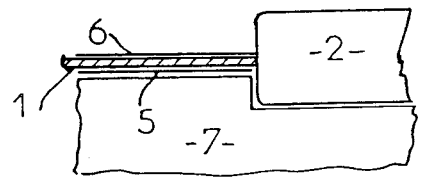
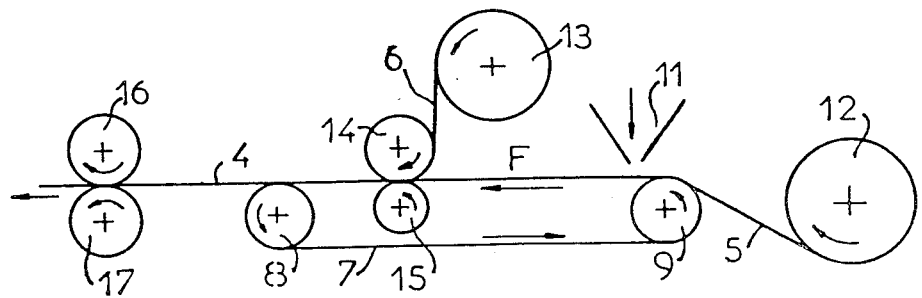

METHOD FOR PACKAGING STERILE ACUPUNCTURE NEEDLES

This invention concerns acupuncture needles, and deals more specifically with the arrangement and packaging of disposable acupuncture needles which may be discarded after use. Except in special cases where gold- or silver-tipped needles may be used, the acupuncture needles routinely utilized today consist of the needle proper, made of steel, which is mounted on a small handle. The needle must be fine and sharply pointed. After use, the needle must be carefully disinfected before any reuse. Obviously, any dull or bent needles must be eliminated.

The aim of the invention is to facilitate use of the needles by acupuncture doctors by sparing them the bother of sterilization, putting new needles in perfect condition at his disposal each time, and facilitating the act of picking up several needles at once. The doctor is frequently required to apply several needles to the same patient, often more than three. Under these circumstances, the acupuncture doctor is required to hold several needles at the ready in his hand, while he places the needles one by one, an operation which is complicated by the fact that the needles at the ready must remain sterile and can be held only by the relative small handle.

In accordance with the invention, the sterilization and usage problems mentioned above are avoided by the fact that the needles are presented in the form of a row of parallel needles whose points and most of the needles themselves are hermetically sealed between two airtight packaging strips, and whose handles extend outside the packaging. It is immediately apparent that with such an arrangement, the acupuncture specialist may easily and without taking any precautions hold a row of sterile needles in his hand, detaching only the needle he needs immediately before putting it to use. It is understood that these needles will be discarded after use. Note that the material used, although noble, is quite limited in terms of weight so that the cost price of such needles manufactured on a large scale could make the use of such needles economical because of savings on sterilization (materials and labor). In addition, from the standpoint of the convenience and safety of use, they are quite preferable.

In the embodiment of the invention, the needles are arranged in a row, parallel to one another, with the point and the longest part of the needles at least being wrapped in an airtight and sterile manner between two continuous strips of a paper, plastic film or similar protective strip, while preferably the handle of the needle protrudes beyond the protective strips.

The invention also relates to a machine allowing for the packaging of acupuncture needles as indicated above, said machine being characterized by the fact that it entails:

a continuous strip for feeding the needles in parallel, one after the other;

devices for unrolling a plastic, paper or analogous film on the strip, the film covering a majority of the needle and extending beyond its tip;

devices for unrolling, atop the plastic, paper or analogous film, another strip of a paper or analogous film of more or less the same width;

means of bonding the two strips by means of heating and pressure, sealing the largest portion of the needle between them, particularly its point, in an airtight manner.

The invention will be clarified by the description which follows and makes reference to the attached drawings, in which:

FIG. 1 is a schematic view along arrow I of FIG. 2 of the needle transport strip in the machine.

FIG. 2 is a cross section roughly along plane II—II of FIG. 1.

FIG. 3 is a top view along arrow III of FIG. 1.

FIG. 4 is a schematic view of a machine allowing for the packaging of needles in accordance with the invention.

FIG. 5 is an enlarged view of the circled detail V in FIG. 2, showing the arrangement of an acupuncture needle on its transport strip when the two packaging films are applied on both sides of the needle.

FIG. 6 shows a fragment of a row of needles packaged in accordance with the invention.

In accordance with the procedure and the packaging machine illustrated in the drawings, the acupuncture needles consisting of the needle proper 1 with its handle 2 at the end opposite the point 3 emerge from the machine completely packaged in a row (FIG. 6), the continuity of which is ensured by the continuous packaging strip 4 which wraps part 1 of the needles on both sides. The packaging strip 4 extends well beyond the point 3 of the needles. On the other hand, it is cut off so as to leave the handle 2 of the needle exposed.

The packaging strip 4 is actually made up of two layers, namely a lower layer 5 and an upper layer 6, which are bonded together so as to enclose needle parts 1 in an airtight and sterile manner.

Packaging may be carried out continuously by feeding the bare needles on a conveyor 7 such as, for example, a rubberized belt driven continuously as indicated by the arrows by the drive wheels 8, 9 of the machine. The strip 7 features a series of hollowed-out channels 10 sized such that they house roughly half the handle 2 of a needle. The hollowed-out parts 10 ensure the proper positioning and spacing, both longitudinally and transversely, of the needles laid out in parallel on the strip 7. The needles may be fed from a bin 11, and any automatic or manual device may be provided in order to eliminate needles which are improperly positioned or to fill any positions which might be left empty.

As the conveyor 7 advances and leads the needles in the direction of arrow F, the lower packaging strip 5 is unwound from a supply wheel 12 at the same speed as the conveyor 7 and in a width roughly the same as the length of part 1 constituting the needle proper (FIG. 3). In the same manner, the upper packaging sheet 6 is unwound and fed from a supply wheel 13. The two sheets 5 and 6 are pressed between two rollers 14, 15 which are turning at the same speed as the belt 7 is being driven. Preferably, the rollers 14, 15 are heated so that they not only drive the strips 5, 6, but thermally bond them. In this case, the nature of the materials used for the strips 5, 6 is obviously selected so as to permit this bonding and then ensure maintenance of the sterile character of the packaging.

Sterilization may be achieved either solely by virtue of the heat bonding of the two films, or may be complemented by other means such as passing the row of needles through a device generating ultraviolet or gamma rays.

Preferably, at the output end of the device there are two additional cogged wheels 16 and 17 revolving synchronously with the advance of the strip, making serrations in the packaging as visible at 18 in FIG. 6 so as to facilitate detaching the needles from the row one by one.

The rows of needles may then be grouped in small boxes holding a suitable quantity, for example 20, 50 or 100 needles.

At the moment of use, the acupuncture specialist will break off a short length of the row and will thus be able to hold in one hand, without difficulty, a reserve of brand new sterile needles ready for use. He need only remove the needles as he needs them.

The invention is not, of course, limited to the mode of execution and arrangement illustrated, which has been provided by way of example only; to the contrary, all technical equivalents of the methods described, as well as combinations thereof, are covered if carried out in the spirit and within the framework of the following claims.

I claim:

1. A method for packaging sterile acupuncture needles having thin needle and enlarged handle portions, the method comprising the steps:

covering only parallel adjacent needle portions with a first continuous strip of material so that the handle portions remain exposed;

depositing a second continuous strip of material over only the needle portions, in overlying relation with the first strip thereby retaining exposure of the handle portion;

bonding the strips together for hermetically sealing the needles in a permanently sterile continuous package;

forming serrations in the package, between each adjacent needle, for maintaining the needles in a continues connected package which permits folding of the packaged needles along the serrations and tearing of any desired number of packaged needles from the remaining continuous package; and whereby the adhesion between the strips and the material is low enough so that individual needles are removable from the package by grasping their handle portions and pulling them from the package.

2. The method set forth in claim 1 wherein the step of positioning the needles on the first continuous strip is preceded by the step of depositing the needles on conveying means having parallel adjacent recesses formed therein for receiving the needle handles.

* * * * *